United States Patent [19]

Ferris

[11] 4,341,793
[45] Jul. 27, 1982

[54] SECONDARY AMINES AND THEIR USE IN PHARMACEUTICAL COMPOSITIONS

[75] Inventor: Michael J. Ferris, Sutton, England

[73] Assignee: Beecham Group Limited, England

[21] Appl. No.: 204,846

[22] Filed: Nov. 7, 1980

[30] Foreign Application Priority Data

Nov. 15, 1979 [GB] United Kingdom ................. 7939536

[51] Int. Cl.³ ................. A61K 31/365; C07D 307/88; A61K 31/34; C07D 307/81
[52] U.S. Cl. .................................. 424/279; 424/285; 549/305; 549/467
[58] Field of Search .................... 260/346.73, 343.3 R; 424/285, 279

[56] References Cited

U.S. PATENT DOCUMENTS 3,452,052  6/1969  Binon et al. .................... 260/346.73
4,221,815  9/1980  Weyer et al. ................. 260/345.7 R

*Primary Examiner*—Henry R. Jiles
*Assistant Examiner*—Bernard Dentz
*Attorney, Agent, or Firm*—Jacobs & Jacobs

[57] ABSTRACT

Compounds of formula (III):

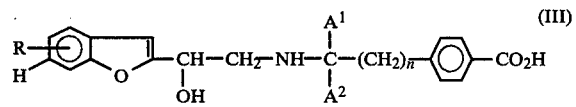

and esters, amides and pharmaceutically acceptable salts thereof, wherein
$A^1$ is hydrogen or methyl;
$A^2$ is hydrogen or methyl;
n is 1, 2 or 3; and
R is hydrogen, chlorine, bromine, hydroxy, nitro, amino or trifluoromethyl,
are useful as anti-hyperglycaemic agents and/or anti-obesity agents.

10 Claims, No Drawings

SECONDARY AMINES AND THEIR USE IN PHARMACEUTICAL COMPOSITIONS

The present invention relates to a group of secondary amine derivatives that possess anti-obesity and/or anti-hyperglycaemic properties, to the method of their preparation and to their use as anti-obesity and/or anti-hyperglycaemic agents when formulated into a pharmaceutical composition.

Certain of the compounds within the formula (I):

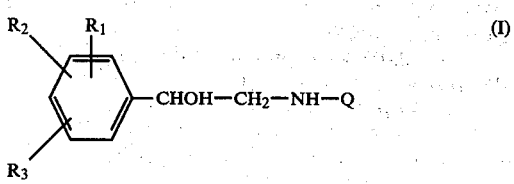

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D T Collins et al, *J Med Chem*, 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Patent No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and/or anti-hyperglycaemic properties. Such compounds may thus be used in the treatment of obesity or hyperglycaemia and can be envisaged as being of particular interest in conditions such as maturity onset diabetes where obesity is often linked with hyperglycaemia. European Patent Application No. 79301197.4 provided the compounds of the formula (II):

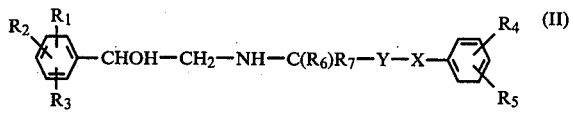

or a pharmaceutically acceptable salt thereof wherein $R_1$ $R_2$ and $R_3$ are as defined in relation to formula (I); $R_4$ is a carboxylic acid group or a salt, ester or amide thereof; $R_4$ is a carboxylic acid group or a salt, ester or amide thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, ethyl or propyl group; $R_7$ is a hydrogen atom or a methyl, ethyl or propyl group; X is an oxygen atom or a bond; and Y is an alkylene group of up to 6 carbon atoms or a bond. Such compounds were shown to have desirable anti-obesity and hyperglycaemic activity. Replacement of the $C_6H_2R_1R_2R_3$ moiety by heteroaromatic moieties such as furyl has been found to result in loss of activity. It is therefore of particular surprise that it has now been discovered that a small gropu of compounds outside the scope of formula (II) have good anti-obesity and/or anti-hyperglycaemic properties coupled with a low level of side effects.

The present invention provides the compounds of the formula (III):

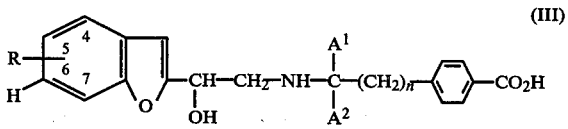

and esters, amides and pharmaceutically acceptable salts thereof, wherein $A^1$ is hydrogen or methyl;
$A^2$ is hydrogen or methyl;
n is 1, 2 or 3; and
R is hydrogen, chlorine, bromine, hydroxy, methoxy, nitro, amino or trifluoromethyl.

As is apparent from the above formula (III), the 6 position of the benzofuranyl groups may not be substituted.

Preferably $A^1$ is methyl. Preferably $A^2$ is hydrogen. Preferably n is 1.

From the foregoing it will be appreciated that preferred compounds of this invention include the compound of the formula (IV):

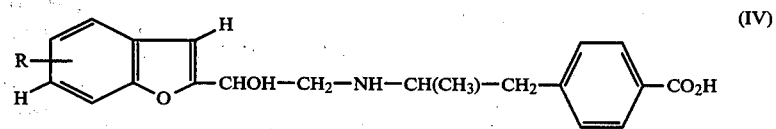

and esters, amides and pharmaceutically acceptable salts thereof.

Preferably R is hydrogen in compounds of formulae (III) and (IV).

Particularly preferred compounds are those of formula (IV) and esters, amides and pharmaceutically acceptable salts thereof, wherein R is a hydrogen atom.

The esters of the compounds of the formulae (III) and (IV) may be any set forth as suitable in the aforementioned European Application which, together with U.S. Ser. No. 51,440, incorporated herein by reference.

Therein $R_4$ is a carboxylic acid group or a salt, ester or amide thereof and apt values of $R_4$ include those of sub-formulae (a)-(c):

$CO_2H$        (a)

$CO_2-(1/q)A^{q+}$        (b)

$CO_2R_8$        (c)

wherein $R_8$ is a group such that $CO_2R_8$ is an ester group. $R_4$ is preferably one of the sub-formulae (a)-(c). An especially favored value for $R_4$ is that of sub-formulae (c). In such compounds it is suitable that $R_8$ is such that the ester group is hydrolysed in-vivo to yield the corresponding compound in which $R_4$ is a group of sub-formulae (a). Particularly suitable values for $R_8$ include lower alkyl groups, wherein "lower" means a group of not more than 4 carbon atoms, substituted by a hydroxyl group not on the α-carbon atom and groups of sub-formulae (f) or (g):

$-CHR_{11}-O-CO-R_{12}$        (f)

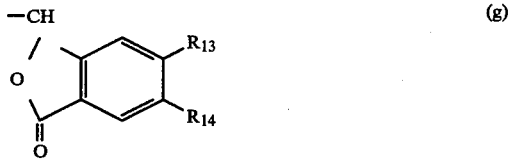

(g)

wherein $R_{11}$ is a hydrogen atom or methyl, $R_{12}$ is lower alkyl or phenyl, $R_{13}$ is hydrogen, methyl or methoxyl and $R_{14}$ is a hydrogen atom, or methyl or methoxyl. Certain particularly suitable values for $R_8$ include methyl, ethyl, propyl and butyl, for example, methyl, ethyl and isopropyl.

Particularly apt esters of the compounds of the formulae (III) and (IV) include lower alkyl esters such as the methyl, ethyl, isopropyl and n-propyl esters.

A preferred ester of the compounds of the formulae (III) and (IV) is the methyl ester.

Esters of the compounds of the formulae (III) and (IV) are preferably provided in the form of an acid addition salt with a pharmaceutically acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acid.

Suitable amides of compounds of formula (III) are those comprising an amino, mono- or di-($C_{1-6}$) alkyl amino moiety. Preferred amides are those comprising an amino or methylamino moiety.

The compounds of the formula (III) have a centre of asymmetry at the carbon atom marked with a single asterisk in formula (IIIa):

wherein R, $A^1$ and n are as defined in relation to formula (III). The compounds of the formula (III) have another centre of asymmetry at the carbon atom marked with two asterisks in formula (IIIa) when $A^1$ is a methyl group.

The present invention extends to the individual stereoisomeric forms of the compounds of the formula (III) as well as to mixtures thereof. Aptly those compounds of the formula (III) which contain two asymmetric centres are provided in the form of the separated diastereoisomers. Such separated diastereoisomers will of course contain a pair of compounds which are mirror images of each other.

X-Ray analysis may be used to determine and correlate absolute stereochemistry.

It has been observed that in the $^{13}C$ NMR spectrum of a compound containing a methyl group on the carbon atom α to the nitrogen atom (ie one existing in diastereoisomeric forms), the R*, R**; S*, S** diastereoisomer is that in which the methyl group appears at higher field (lower numerical value when expressed in ppm, typically <20 ppm downfield from tetramethylsilane) in $d_6$DMSO solution, whilst the lower field (higher numerical value, typically ≧20 ppm downfield from TMS) resonance is attributable to the R*, S**; S*, R** modification. The amount of each diastereoisomer may be estimated from the relative intensities of the absorption lines and is expressed in the examples as a ratio (R* R**, S* S**: R* S**, S* R**). Other paired resonances can occur for the carbon atoms attached directly to the nitrogen atom and the carbon β to nitrogen which carries the hydroxyl group.

The diastereoisomer ratio of said compounds may also be determined by the following gc technique.

To 250 μl of a solution of t-butyldimethylsilyl chloride (0.083 g) and imidazole (0.038 g) dissolved in pyridine (1 ml) was added the compound (~0.001 g) and the solution heated 1 h at 135° C. To this silylated mixture was added trifluoroacetylimidazole (25 μl) and the whole further heated for 0.5 h at 135° C.

0.2 μl of this solution was injected onto a 25 m OVI capillary column contained in a Carlo Erba 4160 Gas Chromatograph under the following conditions.

| | |
|---|---|
| Temperature of Injection block | 250° |
| Oven Temperature | 240° |
| Carrier Gas - Hydrogen at 2 ml/min through column | |
| Split Ratio | 10:1 |

The diastereoisomers elute after about 25 mins and the ratio is determined by area integration using the spectrophysics SP-4000 data system.

The present invention also provides a pharmaceutical composition which comprises a compound of this invention and a pharmaceutically acceptable carrier.

The compositions of this invention will normally be formulated for oral administration although composition formulated for non-oral modes of administration, for example, injection, are also envisaged.

(IIIa)

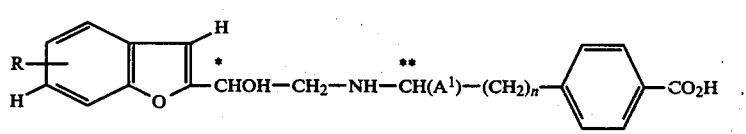

Particularly suitable oral dosage forms are unit dose forms such as tablets or capsules. Other fixed unit dose forms such as powders presented in sachets may also be used.

In accordance with convention pharmaceutical practice the carrier may comprise a diluent, binder, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.01 to 100 mg, more usually 0.2 to 50 mg and favourably 0.5 to 20 mg. Such doses may be taken one to six times a day in a manner such that the total daily dose for a 70 kg adult will generally be about 0.1 to 100 mg and more usually about 2 to 80 mg. The more potent preferred compounds will generally be in unit doses containing 0.1 to 10 mg and more usually 0.25 to 5 mg. Their daily dose will generally be about 0.5 to 20 mg, more usually 1 to 10 mg, for example 2 to 5 mg.

In addition to use in human medicine the compositions of this invention may be used to treat obesity in domestic mammals such as dogs. In general, administration to domestic mammals may be by mouth and will usually take place one or two times a day at about 0.025 mg/kg to 2.5 mg/kg, for example 0.1 mg/kg to 2 mg/kg.

The present invention also provides a process for the preparation of a compound of formula (III) wherein $A^2$ is hydrogen which comprises reducing a compound of the formula (VI)

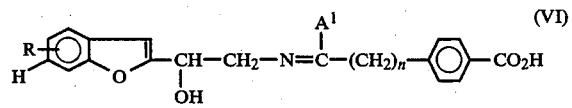

(VI)

or a salt, ester or amide thereof, wherein $A^1$, R and n are as defined in relation to formula (III).

The reduction of the compound of formula (VI) may be effected by catalytic hydrogenation. Suitable catalysts include palladium on charcoal or platinum, for example as platinum oxide. A medium or high pressure of hydrogen gas may be used if palladium is the catalyst but it is generally preferred to use a pressure of hydrogen of about 50–100 psi. If platinum is used as catalyst hydrogen may be employed at about 1 atmosphere pressure. The reaction may be carried out at any convenient non-extreme temperature but it is generally most suitable to use a slightly raised temperature such as 30° C. to 100° C., for example 40° C. to 80° C. The hydrogenation may be carried out in conventional hydrogenation solvent such as a lower alkanol, for example ethanol.

The desired compound may be isolated from the reaction mixture by evaporation of the filtered solution. The initially obtained product may be purified by conventional means, for example by chromatography, crystallisation or the like.

The reduction of the compound of formula (VI) may also be effected using a complex hydride such as sodium borohydride.

This reaction is generally carried out in a lower alkanolic solvent, for example methanol. An approximately ambient temperature may be employed, for example 20° C. to 30° C.

The desired compound may be obtained from the reaction mixture by evaporation, extraction into a suitable solvent such as ethyl acetate and evaporation. The initially obtained product may be purified as outlined hereinbefore.

The compound of the formula (VI) may be prepared by the reaction of a compound of the formula (VII)

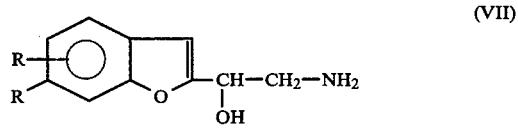

(VII)

with a compound of the formula (VIII)

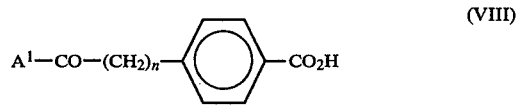

(VIII)

or a salt, ester or amide thereof, wherein $A^1$, R and n are as defined in relation to formula (III).

The reaction is generally carried out under conditions that result in the removal of water formed during the reaction. Thus a convenient method is azeotropically to distill the water from a refluxing benzene solution using a Dean and Stark apparatus.

It is often convenient to prepare the compound of the formula (II) and use it in situ without isolation.

If a racemic mixture of the compound of the formula (VII) is used then the final reaction product of formula (III) is a mixture of all four enantiomers which may be separated by, for example fractional crystallisation into diastereoisomeric pairs. If one enantiomer of the compound of formula (VII) is used, a diastereomeric pair of enantiomers is obtained which may then be separated into individual enantiomers by conventional methods.

The present invention further provides another process for producing the compounds of formula (III) which comprises reacting a compound of the formula (IX)

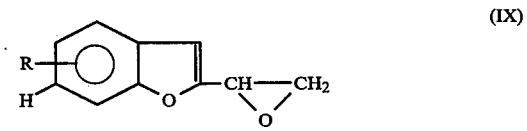

(IX)

with a compound of the formula (X)

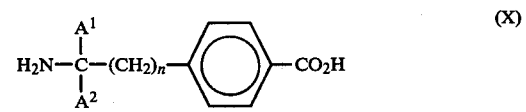

(X)

or a salt, ester or amide thereof, wherein $A^1$, $A^2$, R and n are as defined in relation to formula (III).

This reaction may be carried out in a solvent such as a lower alkanol, preferably ethanol.

By using single enantiomers of the compounds of formulae (IX) and (X), a stereospecific synthesis of single enantiomers of formula (III) may be achieved.

The present invention also provides a further process for producing the compounds of formula (III) which comprises reducing a compound of formula (XI)

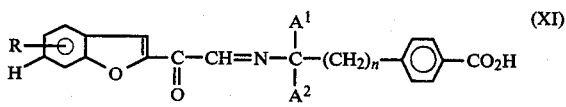

or a salt, ester or amide thereof, wherein A¹, A², R and n are as defined in relation to formula (III).

The reduction of the compound of the formula (XI) may be carried out using a hydride or hydrogen as described for the reduction of the compound of formula (VI).

The compound of formula (XI) may be prepared by the reaction of a compound of the formula (XII)

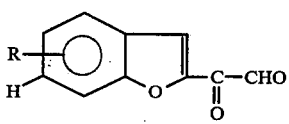

or its hydrate or hemi-acetal of a lower alkanol, with a compound of the formula (X) as defined above.

This reaction is generally carried out under the same conditions as are used for the reaction between compounds of formulae (VII) and (VIII).

The compound of formula (XI) may be obtained from the reaction mixture by evaporation of the solvent and may then be reduced in situ.

By using a racemic mixture of the compound of formula (X), mixtures having similar stereochemistry to those produced by the reaction between compounds of formulae (VII) and (VIII) are obtained.

By using a single enantiomer of the compound of formula (X) a diastereoisomeric pair of enantiomers is obtained which may then be separated into individual enantiomers by conventional methods.

The present invention further provides another process for producing the compounds of formula (III) which comprises reducing a compound of the formula (XIII)

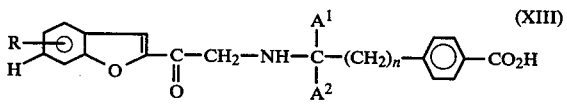

or a salt, ester or amide thereof, wherein A¹, A², R and n are as defined in relation to formula (III).

The reduction of the compound of formula (XIII) may take place as described for reduction of the compound of formula (VI).

The compound of the formula (XIII) may be prepared by the reaction of a compound of the formula (XIV)

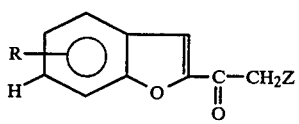

wherein Z is a halogen atom, preferably bromine, with a compound of formula (X) as defined above.

This reaction may be carried out in a solvent such as acetonitrile or butanone at an elevated temperature, for example under reflux.

After completion, the reaction mixture may be diluted with ether, filtered and the filtrate evaporated.

In a modification of the above mentioned process, the N-benzyl derivative of a compound of formula (X) may be used in place of the compound of formula (X), in which case the final reduction/debenzylation is carried out catalytically with palladium on charcoal.

By using a racemic mixture or a single enantiomer of the compound of formula (X), isomeric mixtures similar to those described above may be obtained.

The present invention also provides a still further process for producing a compound of formula (III) which comprises reducing a compound of formula (XV)

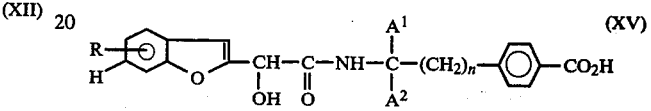

or a salt or ester thereof, wherein A¹, A², R and n are as defined in relation to formula (III), with diborane.

The compound of formula (XV) may be prepared by reacting a compound of the formula (XVI)

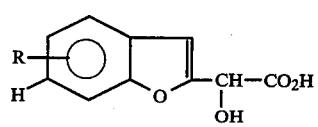

with a compound of formula (X) as defined above. The reaction may take place under standard peptide formation reaction conditions.

By using single enantiomers of the compounds of the formulae (XVI) and (X) a stereospecific synthesis of single enantiomers of formula (III) can be achieved. For example, a compound of formula (XVI) with R absolute configuration and a compound of formula (X) with R absolute configuration would give a compound of formula (III) with the RR configuration.

Esters produced by the above processes may, if desired, be cleaved by conventional means to afford the free acid, and such acids may optionally be esterified by conventional means.

Compounds of formula (III) produced by the above processes may, if desired, be converted to their pharmaceutically accepable salts by conventional means, and such salts may be converted to the free acid, and/or base by conventional means.

Compounds of formula (III) may be purified by conventional methods such as crystallisation and chromatography.

Those compounds of formula (III) having only one asymmetric carbon atom (ie when A¹ and A² are the same) may, if desired, be resolved into enantiomers by conventional means, for example by the use of an optically active acid as a resolving agent. Those compounds of formula (III) having two asymmetric carbon atoms may be separated into diastereoisomeric pairs of enantiomers by, for example fractional crystallisation from a suitable solvent such as ethyl acetate. The pair of enantiomers thus obtained may be separated into individual stereoisomers by conventional means such as by the use of an optically active acid as a resolving agent.

Suitable optically active acids which may be used as resolving agents are described in "Topics in Stereochemistry" Vol 6, Wiley Intersecience, 1971; Allinger N L and Eliel, W L Eds.

Any enantiomer of a compound of formula (III) may be obtained by stereospecific synthesis using optically pure starting material of known configuration.

The present invention further provides an intermediate, useful in the production of a compound of formula (III), which intermediate is a compound of formulae (VI), (XI), (XIII), (XV) or (XVI) as hereinbefore defined, provided that R is other than hydrogen.

The compounds of this invention may be prepared by the processes of the aforementioned incorporated European and U.S. Patent Applications. A particularly apt method comprises the reaction of an appropriate benzofuranylglyoxal with an ester of a compound of the formula (V):

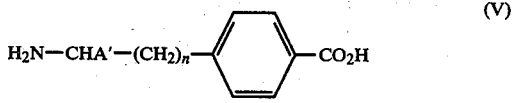
(V)

wherein A' and n are as defined in relation to formula (III) reducing the resulting compound and thereafter if desired cleaving said ester and/or salifying the product.

This initial reaction is generally carried out under conditions that result in the removal of water formed during the reaction. A convenient method is to azeotropically remove the water from a refluxing benzene solution using a Dean and Stark apparatus. The reduction is generally carried out in a lower alkanol. The benzene is thus removed by evaporation and replaced by the lower alkanol. The reduction may be effected with a borohydride such as sodium borohydride. The product may be obtained from the reaction mixture by evaporation of the solvent and after washing may be purified chromatographically if desired.

The processes of European Application No 79301197.4, Japanese Application No 82545/79 and US Application Serial No 51 440 are incorporated herein by cross reference.

The following Examples illustrates the invention.

EXAMPLE 1

2-(2-Benzofuranyl)-N-[2-(4-carbomethyoxyphenyl)-1-methylethyl]-2-hydroxyethanamine A mixture of 2-(4-carbomethoxyphenyl)-1-methylethanamine (2.2g) and 2-benzofuranylglyoxal (2.2 g) in dry benzene (100 ml) was refluxed under a Dean and Stark head until the theoretical amount of water had been collected (about 2h). The solvent was evaporated and methanol (100 ml) was added. The solution was cooled in ice during the portionwise addition of sodium borohydride (5.0 g) after which the solution was stirred at room temperature for 3h. The solvent was evaporated and the residue was partitioned between water (100 ml) and chloroform (100 ml). The aqueous phase was extracted with further chloroform (100 ml) and the combined organic extracts were dried over anhydrous magnesium sulphate. The solvent was evaporated and the residue was crystallised from methanol to give colourless crystals of the title compound m.p. 115°–122° shown to be a mixture of diastereoisomers by $^{13}$C NMR: $^{13}$C nmr (d$_6$ DMSO): 19.86 ppm. (20%), 20.00 ppm (80%). $^1$H nmr $\tau$ (d$_6$ DMSO): 9.05 (3H, d, J=6 Hz), 6.70–7.60 (6H, m), 6.19 (3H, s), 5.27 (1H, m), 4.42 (1H, br), 3.29 (1H, s), 2.3–2.9 (6H, m), 2.19 (2H, d, J=8 Hz).

Recrystallisation from ethyl acetate gave a sample mp 123–124 shown by gc to be a 7:93 ratio of diastereoisomers. $^{13}$C nmr (DMSO d$_6$) 20.1 ppm. Evaporation of the mother liquor and chromatography on Kieselgel 60 (2% methanol-chloroform) gave an oil which was crystallised twice from ethyl acetate to give a sample mp 88° shown by gc to be a 91:9 ratio of diastereoisomers. $^{13}$C nmr (DMSO d$_6$) 19.9 ppm. 1H nmr of both samples identical with that of the 20:80 mixture.

EXAMPLE 2

2-(2-Benzofuranyl)-N-(2-[4-carbomethoxyphenyl]ethyl)-2-hydroxyethanamine

The title compound was obtained by the procedure of Example 1 replacing 2-(4-carbomethoxyphenyl)-1-methylethanamine by 2-(4-carbomethoxyphenyl)ethanamine. The crude oil was chromatographed on Kieselgel 60 (2% methanol-chloroform) and crystallised from ethyl acetate to give 2-(2-benzofuranyl)-N-(2-[4-carbomethoxyphenyl]ethyl)-2-hydroxyethanamine, m.p. 117°–119° C.

'Hnmr$\tau$(CHCl$_3$) 7.61 (2H, broad, disappears on D$_2$O), 7.4–6.7 (6H, m), 6.08 (3H, s), 5.18 (1H, t, J=6 Hz), 3.37 (1H, s), 3.0–2.3 (6H, m), 2.06 (2H, d, J=8 Hz).

EXAMPLE 3

2-(2-Benzofuranyl)-N-(2-[4-carbomethoxyphenyl]-1,1-dimethylethyl)-2-hydroxyethanamine The title compound was obtained by the procedure of Example 1, replacing 2-(4-carbomethoxyphenyl)-1-methylethanamine by 2-(4-carbomethoxyphenyl)-1,1-dimethylethanamine. The crude oil was chromatograhed on Kieselgel 60 (2% methanol-chloroform) and crystallised from hexane to give 2-(2-benzofuranyl)-N-(2-[4-carbomethoxyphenyl]-1,1-dimethylethyl)-2-hydroxyethanamine, mp 127°–129° C.

'Hnmr$\tau$(CDCl$_3$): 8.92 (6H, d, J=6 Hz), 7.92 (2H, broad, disappears on D$_2$O), 7.25 (2H, s), 6.9 (2H, d, J=7 Hz), 6.1 (3H, s), 5.2 (1H, t, J=7 Hz), 3.35 (1H, s), 2.87–2.3 (6H, m), 2.2 (2H, d, J=8 Hz).

EXAMPLE 4

2-(2-Benzofuranyl)-N-(2-[4-N'-methylcarboxamidophenyl]-1,1-dimethylethyl)-2-hydroxyethanamine 2-(2-Benzofuranyl)-N-(2-[4-N'-methylcarboxamidophenyl]-1,1-dimethylethyl)-2-hydroxyethanamine, m. 165°–167° C. (ethyl acetate) was obtained by the procedure of Example 1 replacing 2-(4-carbomethoxyphenyl)-1-methylethanamine by 2-(4-N-methylcarboxamidophenyl)-1,1-dimethylethanamine.

'Hnmr$\tau$(DMSO d$_6$) 9.03 (6H, s), 8.57 (1H, broad, disappears with D$_2$O), 7.31 (2H, s), 7.21 (3H, s, J=6 Hz, collapses to singlet on D$_2$O), 7.03 (2H, d, J=6 Hz), 5.28 (1H, m), 4.4 (1H, d, J=6 Hz, disappears on D$_2$O), 3.24 (1H, s), 3.0–2.61 (4H, m), 2.61–2.18 (4H, m), 1.7 (1H, q, J=6 Hz, disappears on D$_2$O).

EXAMPLE 5

2-(2-Benzofuranyl)-N-(3-[4-carbomethoxyphenyl]-1-methylpropyl)-2-hydroxyethanamine The title compound was obtained by the procedure of Example 1, replacing 2-(4-carbomethyoxyphenyl)-1- methylethanamine by 3-(4-carbomethoxyphenyl)-1-methylpropanamine. The crude oil was chromatographed on Kieselgel 60 (2% methanol-chloroform) and crystallised from benzene-hexane to give 2-(2-benzofuranyl)-N-(3-[4-carbomethoxyphenyl]-1-methylpropyl)-2-hydroxyethanamine, mp 104°–108° C. (<10:>90 ratio of diastereoisomers).

'Hnmrτ(CDCl$_3$) 8.83 (3H, d, J=6 Hz), 8.5–8.0 (2H, m), 7.83 (2H, broad, disappears with D$_2$O), 7.5–7.25 (2H, m), 7.0–6.7 (3H, m), 6.07 (3H, s), 5.12 (1H, t, J=7 Hz), 3.31 (1H, s), 2.9–2.34 (6H, m), 2.04 (2H, d, J=8 Hz).

EXAMPLE 6

2-(2-Benzofuranyl)-N-(3-[4-carbomethoxyphenyl]-1,1-dimethylpropyl)-2-hydroxyethanamine The title compound was obtained by the procedure of Example 1, replacing 2-(4-carbomethoxyphenyl)-1-methylethanamine by 3-(4-carbomethoxyphenyl)-1,1-dimethylpropanamine. The crude oil was chromatographed on Kieselgel 60 (2% methanol-chloroform) and crystallised from ethyl acetate to give 2-(2-benzofuranyl)-N-(3-[4-carbomethoxyphenyl]-1,1-dimethylpropyl)-2-hydroxyethanamine, mp 141°–145° C.

'Hnmrτ(DMSO d$_6$): 8.93 (6H, s), 8.67–8.17 (2H, m), 7.6–7.3 (2H, m), 7.09 (2H, d, J=7 Hz), 6.7 (1H, broad, disappears on D$_2$O), 6.17 (3H, s), 5.28 (1H, t, J=7 Hz), 4.4 (1H, broad, disappears on D$_2$O), 3.21 (1H, s), 3.0–2.4 (6H, m), 2.1 (2H, d, J=8 Hz).

EXAMPLE 7

2-(2-Benzofuranyl)-N-(3-[4-carboxamidophenyl]-1,1-dimethylpropyl)-2-hydroxyethanamine 2-(2-Benzofuranyl)-N-(3-[4-carboxamidophenyl]-1,1-dimethylpropyl)-2-hydroxyethanamine, mp 170°–173° C. (ethyl acetate) was obtained as a monohydrate by the procedure of Example 1, replacing 2-(4-carbomethoxyphenyl)-1-methyl ethanamine by 3-(4-carboxamidophenyl)-1,1-dimethylpropanamine.

'Hnmrτ(DMSO d$_6$): 8.93 (6H, s), 8.7–7.2 (2H,m), 7.7–7.3 (2H,m), 7.1 (2H,d,J=7 Hz), 6.7 (2H, broad, disappears on D$_2$O), 5.28 (1H,t,J=7 Hz), 4.5 (2H, broad, disappears on D$_2$O), 3.21 (1H, s), 3.0–2.6 (4H, m), 2.5–2.3 (2H, m), 2.21 (2H, d, J=8 Hz).

EXAMPLE 8

2-(2-Benzofuranyl)-N-(3-[4-N'-methylcarboxamidophenyl]-1,1-dimethylpropyl)-2-hydroxyethanamine 2-(2-Benzofuranyl)-N-(3-[4-carbomethoxyphenyl]-1,1-dimethylpropyl)-2-hydroxyethanamine (1.0 g) was dissolved in methanolic methylamine (15 ml) and heated at 110° in an autoclave for 5h. The solvent was evaporated and the residue recrystallised from ethyl acetate to yield 2-(2-benzofuranyl)-N-(3-[4-N'-methylcarboxamidophenyl]-1,1-dimethylpropyl)-2-hydroxyethanamine (0.65 g) mp 134°–137° C.

'Hnmrτ(DMSO d$_6$): 8.93 (6H, s), 8.5–8.3 (2H, m), 7.5–7.7 (2H, m), 7.3 (3H, d, J=4 Hz, collapses to singlet on D$_2$O), 7.1 (2H, d, J=6 Hz), 6.7 (2H, broad, disappears on D$_2$O), 5.3 (1H, t, J=6 Hz), 3.23 (1H, s), 2.9–2.61 (4H, m), 2.57–2.37 (2H,m), 2.24 (2H, d, J=8 Hz), 1.7 (1H, q, J=4 Hz).

EXAMPLE 9

2-(2-Benzofuranyl)-N-(3-[4-carbomethoxyphenyl]-propyl)-2-hydroxyethanamine

The title compound was prepared in an identical manner to that described in Example 1, replacing 2-(4-carbomethoxyphenyl)-1-methylethanamine by 3-(4-carbomethoxyphenyl) propanamine. Chromatography on Kieselgel 60 (2% methanol-chloroform) gave 2-(2-benzofuranyl)-N-(3-[4-carbomethoxyphenyl]propyl)-2-hydroxyethanamine, mp 122°–124° C. (benzenehexane).

'Hnmrτ(CDCl$_3$+d$_6$ DMSO), 8.4–7.9 (2H, m), 7.5–7.15 (4H,m), 6.95 (2H, d, J=6 Hz), 6.5 (2H, broad, disappears on D$_2$O), 6.1 (3H, s), 5.13 (1H, t, J=6 Hz), 3.4 (1H, s), 2.9–2.4 (6H, m), 2.1 (2H, d, J=8 Hz).

EXAMPLE 10

N-[2-(4-Carbomethoxyphenyl)-1-methylethyl]-2-[2-(5-chlorobenzofuranyl)]-2-hydroxyethanamine A mixture of 2-(4-carbomethoxyphenyl)propanone (3.17 g) and 2-[2-(5-chlorobenzofuranyl)]-2-hydroxyethanamine, (3.49 g) in benzene was heated under reflux using a Dean and Stark head until the theoretical amount of water had been collected. The solvent was evaporated, the residue taken up in ethanol and platinum oxide added. The solution was hydrogenated at ambient temperature. The catalyst was removed by filtration through celite and the filtrate evaporated. The residue was chromatographed on Kieselgel 60. Elution with 2% methanol-chloroform gave N-[2-(4-carbomethoxyphenyl)-1-methylethyl]-2-[2-(5-chlorobenzofuranyl)]-2-hydroxyethanamine (2.5 g) as a 59:41 mixture of diastereoisomers, mp 100°–102° C. (hexane).

'Hnmrτ(d$_6$ DMSO), 9.1 (3H, d, J=6 Hz), 8.4 (1H, broad), 7.32 (2H, d, J=6 Hz), 7.3–7.0 (3H, m), 6.19 (3H, s), 5.3 (1H, t, J=6 Hz), 4.4 (1H, broad), 3.32 (1H, s), 2.85–2.35 (5H, m), 2.25 (2H, d, J=8 Hz).

EXAMPLE 11

N-[2-(4-Carbomethoxyphenyl)-1-methylethyl]-2-[2-(5-methoxybenzofuranyl)]-2-hydroxyethanamine N-[2-(4-Carbomethoxyphenyl)-1-methylethyl]-2-[2-(5-methoxybenzofuranyl)]-2-hydroxyethanamine, mp 116°–117° C. (ether) was prepared as a 53:47 mixture of diastereoisomers in an identical manner to that described in Example 10, replacing 2-[2-(5-chlorobenzofuranyl)]-2-hydroxyethanamine by 2-[2-(5-methoxybenzofuranyl)]-2-hydroxyethanamine.

'Hnmrτ(d$_6$ DMSO), 9.1 (3H, d, J=6 Hz), 8.4 (1H, broad), 7.35 (2H, d, J=6 Hz), 7.3–7.0 (3H, m), 6.25 (3H, s), 6.2 (3H, s), 5.35 (1H, t, J=6 Hz), 4.5 (1H, broad, disappears with D$_2$O), 3.45 (1H, s), 3.2 (1H, dd, J=8 Hz, J=2 Hz), 2.95 (1H, d, J=2 Hz), 2.75 (2H, d, J=8 Hz), 2.65 (1H, d, J=8 Hz), 2.25 (2H, d, J=8 Hz).

EXAMPLE 12

N-[2-(4-Carbomethoxyphenyl)-1-methylethyl]-2-[7-methoxybenzofuranyl)]-2-hydroxyethanamine N-[2-(4-Carbomethoxyphenyl)-1-methylethyl]-2-[7-methoxybenzofuranyl)]-2-hydroxyethanamine, mp 106°–108° C., (ether) was prepared as a 69:31 mixture of diastereoisomers in an identical manner to that described in Example 10, replacing 2-[2-(5-chlorobenzofuranyl)]-2-hydroxyethanamine by 2-[2-(7-methoxybenzofuranyl)]-2-hydroxyethanamine.

'Hnmrτ(d₆ DMSO) 9.1 (3H, d, J=6 Hz), 8.5 (1H, broad, disappears with D₂O), 7.3 (2H, d, J=6 Hz), 7.2-7.0 (3H, m), 6.18 (3H, s), 6.19 (3H, s), 5.2 (1H, t, J=6 Hz), 4.45 (1H, broad, disappears with D₂O), 3.35 (1H, s), 3.25-3.05 (1H, m), 3.0-2.85 (2H, m), 2.75 (2H, d, J=8 Hz), 2.2 (2H, d, J=8 Hz).

EXAMPLE 13

2-[2-(5-Bromobenzylfuranyl)]-N-[2-(4-carbomethoxyphenyl)-1-methylethyl]-2-hydroxyethanamine 2-[2-(5-Bromobenzofuranyl)]-N-[2-(4-carbomethoxyphenyl)-1-methylethyl]-2-hydroxyethanamine, mp 110° C. (hexane), was prepared as a 47:53 mixture of diastereoisomers, as described in Example 10, replacing 2-[2-(5-chlorobenzofuranyl)]-2-hydroxyethanamine by 2-[2-(5-bromobenzofuranyl)]-2-hydroxyethanamine. Sodium borohydride in methanol was used to reduce the imine instead of hydrogenation over platinum.

'Hnmrτ(d₆DMSO), 9.1 (3H, d, J=6 Hz), 8.5-8.0 (1H, broad), 7.3 (2H, d, J=6 Hz), 7.25-6.9 (3H, m), 6.2 (3H, s), 5.3 (1H, t, J=6 Hz), 3.4 (1H, s), 2.8 (2H, d, J=8 Hz), 2.55 (2H, m), 2.2 (1H, s), 2.15 (2H, d, J=8 Hz).

EXAMPLE 14

(1R, 2'R); (1R, 2'S)-2'-(2-Benzofuranyl)-N-[2-(4-carbomethoxyphenyl)-1-methylethyl]-2'-hydroxyethanamine The title compound was prepared as described in Example 1, replacing 2-(4-carbomethoxyphenyl)-1-methylethanamine by 1R-2-(4-carbomethoxyphenyl)-1-methylethanamine. After chromatography on Kieselgel 60 in 2% methanol-chloroform the crude oil was crystallised from ethyl acetate and recrystallised again from the same solvent to give crystals of (1R2'S)-2'-(2-benzofuranyl)-N-[2-(4-carbomethoxyphenyl)-1-methylethyl]-2'-hydroxyethanamine, mp 107°-109° C., 99% enantiomeric purity by gc. The original mother liquor was evaporated and recrystallised twice from ethyl acetate to yield further crops of the (1R,2'S) enantiomer. The mother liquor from the last crop was then shown to be of (80:20) diastereoisomer ratio (by gc). Treatment of this in ether with ethereal hydrogen chloride gave the salt which was recrystallised from ethanol-ether to give (1R,2'R)-2'-(2-benzofuranyl)-N-[2-(4-carbomethoxyphenyl)-1-methylethyl]-2'-hydroxyethanamine hydrochloride, mp 167°-169° C., 96% enantiomeric purity by gc.

EXAMPLE 15

2-(2-Benzofuranyl)-N-(3-[4-N'-methylcarboxamidophenyl]propyl)-2-hydroxyethanamine 2-(2-Benzofuranyl)-N-(3-[4-N'-methylcarboxamidophenyl]propyl)-2-hydroxyethanamine was prepared as the hydrochloride salt, mp 135°-6° C. (ethyl acetate) in an identical manner to that described in Example 8, replacing 2-(2-benzofuranyl)-N-(3-[4-carbomethoxyphenyl]-1,1-dimethylpropyl)-2-hydroyethanamine by 2-(2-benzofuranyl)-N-(3-[4-carbomethoxyphenyl]propyl)-2-hydroxyethanamine.

'Hnmr (DMSO d₆) 8.4-8.1 (2H, m), 7.6-7.0 (9H, m), 7.0-5.5 (2H, broad), 5.2 (1H, t, J=6Hz), 3.3 (1H, s), 2.85-2.7 (4H, m), 2.6-2.35 (2H, m), 2.25 (2H, d, J=8Hz), 1.75 (1H, q, J=6Hz).

PREPARATION 1

2-Benzofuranylglyoxal

A mixture of 2-acetylbenzofuran (100 g) and selenium dioxide (69.3 g) was dissolved in water (20 ml) and dioxan (500 ml) and heated under reflux for 24 h. The reaction mixture was filtered and the solvent evaporated to give a dark-red solid which was taken up in dimethylformamide and heated on a steam bath for 8 h. The solution was filtered, the solvent evaporated and the residue triturated with ether to give the title compound (65.4 g).

'Hnmr≈(DMSO d₆), 4.0 (1H, s), 3.0-2.0 (4H, m), 1.95 (1H, s).

PREPARATION 2

The substituted 2-benzofuranyl-2-hydroxy ethanamines described in Examples 10, 11, 12 and 13 were made in an identical manner typified by the procedure for the preparation of 2-[2-(5-chlorobenzofuranyl)]-2-hydroxyethanamine given below.

2-[2-(5-Chlorobenzofuranyl)]-2-hydroxyethanamine

Trimethylsilylcyanide (3.75 ml) was added dropwise under nitrogen to a solution of 5-chloro-2-formyl benzofuran (prepared as described in Ste Produits Chimiques due Marly, French Pat. No. 1 537 2 06-21-7-1967) (5.0 g) containing a trace of zinc iodide in dry ether at 0° C. After the end of addition the solution was allowed to stir at ambient temperature for 12 h. The solution was then transferred to a dropping funnel and added dropwise to a suspension of lithium aluminium hydride (1.16 g) in ether under nitrogen. Water (1.2 ml), 2M sodium hydroxide (1.2 ml) followed by more water (3.6 ml) was added, the solid filtered, washed with chloroform and filtrate evaporated to give a red oily solid which was recrystallised from cyclohexane to give the title compound (3.49 g).

'Hnmr≈(CDCl₃) 7.2 (2H, dd), 8.0-6.0 (3H, broad), 5.45 (1H, t, J=6Hz), 3.3 (1H, s) 2.8 (1H, dd, J=8Hz, J=2Hz), 2.45 (1H, d, J=8Hz), 2.4 (1H, d, J=2Hz).

DEMONSTRATION OF EFFECTIVENESS OF COMPOUNDS (i) Anti-obesity activity

The compounds were administered in water or carboxymethyl cellulose suspension to genetically obese mice by oral gavage daily for 28 days. At the end of this time the carcass composition was determined. The results obtained were as follows:

| Compound of Example | Dose mg/kg p.o. | g-Lipid per Mouse Treated | g-Lipid per Mouse Control |
|---|---|---|---|
| 1 (20:80) | 10 | 13.9 | 17.1 |
| *1 (91:9) | 4.9 | 12.88 | 16.25 |

*15 days (ii) Effect on energy expenditure

The effect of the compound on the energy expenditure of mice was demonstrated by means of the following procedure.

Female CFLP mice each weighing approximately 24 g were given food and water ad lib before and during the experiment. The compounds were dissolved in water by addition of the same number of moles hydrochloric acid, and each solution was administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J B de V Weir (J Physiol (London) (1949) 109, 1-9). The food intake of the mice was measured over this same period of 21 hours. The results are expressed as a percentage of the mean food intake or rate of energy expenditure of the mice dosed with water.

| Compound of Example | Dose mg/kg p.o. | Percentage of Control Values | | |
|---|---|---|---|---|
| | | Energy Expenditure (0-3H) | (0-21H) | Food Intake |
| 1 (91:9) | 10 | 143 | 122 | 91 |
| 1 (7:93) | 10 | 119 | 104 | 93 |
| 1 (20:80) | 20 | 169 | 128 | 100 |
| 2 | 18.9 | 161 | 111 | 102 |
| 3 | 20.4 | 129 | 104 | 101 |
| 5 | 20.4 | 140 | 110 | 103 |
| 9 | 19.7 | 123 | 104 | 107 |
| 12 | 22 | 133 | 107 | 96 |
| 14 (1:99) | 9.8 | 116 | 104 | 88 |
| 14 (96:4) | 9.8 | 158 | 118 | 82 |
| 15 | 19.6 | 135 | 102 | 85 |

(iii) Cardiac activity

Rat hearts were perfused by the Langenforff procedure. Hearts were dissected free within 30 seconds of death and reverse perfuse via the aorta and coronary vessels with Krebs-Ringer bicarbonate solution (pH 7.4, 37° C.) gassed with 95% $O_2$:5% $CO_2$. The flow rate was 8 to 12 mls/minute. Responses were obtained after injection of drug dissolved in isotonic saline into the perfusion media. Heart rate and tension were displayed on an Ormed MX2P recorder via a tension transducer and heart ratemeter.

Results are expressed as a percentage of the response due to salbutamol.

| Compound of Example | Dose Added (μg) | Heart Tension | Heart Rate |
|---|---|---|---|
| 1 (91:9) | 10 | 0 | 22 |
| 1 (7:93) | 30 | 0 | 22 |
| 2 | 10 | 0 | 50 |
| 3 | 30 | 19 | 22 |
| 4 | 30 | 63 | 36 |
| 5 | 10 | 33 | 5 |
| 6 | 10 | 0 | 43 |
| 7 | 10 | 13 | 33 |
| 8 | 10 | 0 | 17 |
| 9 | 10 | 0 | 50 |
| 14 (1:99) | 30 | 25 | 0 |
| 14 (96:4) | 10 | 33 | 75 |
| 15 | 10 | 50 | 17 |

(iv) Hypoglycaemic activity

Female CFLP mice, weighing approximately 25 g, were fasted for 24 hours prior to the study. The compounds under study were administered orally to each of 8 mice. 30 minutes later a blood sample (20 μl) was obtained from the tail for the analysis of blood glucose. Immediately after taking this blood sample, each mouse was given a glucose load (1 g/kg body weight subcutaneously). Further blood samples were then obtained from each mouse at 30 minute intervals for 120 minutes.

Compounds that produced a significant (P=0.05) reduction of blood glucose, compared with control mice given water, at any time interval were considered active. The area under the blood glucose curve over the 2 hour period after giving the glucose load was calculated for each compound and compared with the value for control animals.

| Compound of Example | Dose mg/kg p.o. | Reduction in Area Under Blood Glucose Curve % |
|---|---|---|
| 1 (91:9) | 1.0 | 27.4 |
| 1 (7:93) | 17.7 | 46.4 |
| 2 | 4.2 | 44.7 |
| 3 | 18.4 | 22.2 |
| 4 | 18.3 | 11.5 |
| 5 | 4.6 | 29.9 |
| 6 | 19.1 | 7.1 |
| 7 | 19.2 | 7.8 |
| 8 | 19.0 | 10.8 |
| 9 | 17.7 | 49.3 |
| 10 | 19.4 | 10.4 |
| 11 | 19.2 | 9.6 |
| 12 | 19.4 | 39.2 |
| 13 | 21.6 | 25.4 |
| 14 (1:99) | 17.7 | 53.1 |
| 14 (96:4) | 8.8 | 39.2 |

I claim:

1. A compound of formula (III):

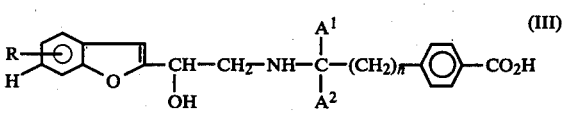

or an ester thereof based on a lower alkanol optionally substituted by a hydroxy group not on the α-carbon atom or alcohols of the formula $HOCHR_{11}-OCO-R_{12}$ and

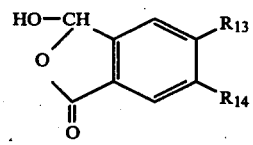

wherein $R_{11}$ is a hydrogen atom or methyl, $R_{12}$ is lower alkyl or phenyl, $R_{13}$ is hydrogen, methyl, or methoxy and $R_{14}$ is hydrogen, methyl, or methoxy, an amide thereof wherein the amide comprises and amino, mono or di-($C_{1-6}$) alkyl amino moiety, or pharmaceutically acceptable salt of the carboxylic acid group, wherein $A^1$ is hydrogen or methyl;
$A^2$ is hydrogen or methyl;
n is 1, 2 or 3; and
R is hydrogen, chlorine, bromine, hydroxy, methoxy, nitro, amino or trifluoromethyl.

2. A compound as claimed in claim 1, wherein R is hydrogen.

3. A compound as claimed in claim 1 or 2 wherein $A^1$ is methyl and $A^2$ is hydrogen.

4. A compound as claimed in claim 1, 2 or 3 wherein n is 1.

5. A pharmaceutical composition having anti-obesity and anti-hyperglycaemic activity comprising a compound of formula (III):

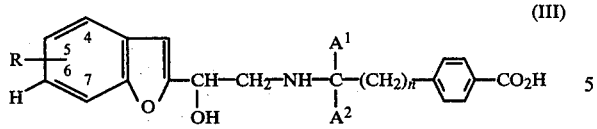

or an ester, amide or pharmaceutically acceptable salt of the carboxylic acid group thereof, wherein
- $A^1$ is hydrogen or methyl;
- $A^2$ is hydrogen or methyl;
- n is 1, 2 or 3; and
- R is hydrogen, chlorine, bromine, hydroxy, methoxy, nitro, amino, or trifluoromethyl, in a therapeutically effective amount, and a pharmaceutically acceptable carrier therefor, the esters and amides being as defined in claim 1.

6. A pharmaceutical composition as claimed in claim 5 in an oral, unit dosage form comprising from 0.01 to 100 mg of a compound of formula (III).

7. A method for treating hyperglycaemia or obesity in humans and domestic mammals comprising the administration of an effective, non-toxic amount of a compound of formula (III):

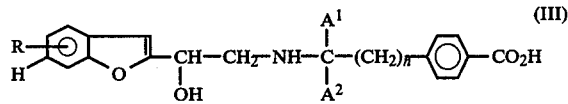

or an ester thereof based on a lower alkanol optionally substituted by a hydroxy group not on the α-carbon atom or alcohols of the formula $HOCHR_{11}-OCO-R_{12}$ and

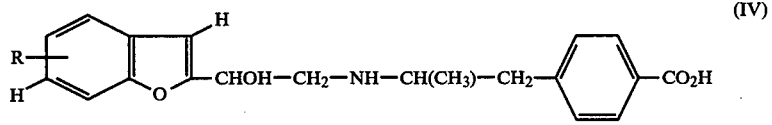

wherein $R_{11}$ is a hydrogen atom or methyl, $R_{12}$ is lower alkyl or phenyl, $R_{13}$ is hydrogen, methyl, or methoxy and $R_{14}$ is hydrogen, methyl, or methoxy, an amide thereof wherein the amide comprises and amino, mono or di-($C_{1-6}$) alkyl amino moiety, or pharmaceutically acceptable salt of the carboxylic acid group, wherein
- $A^1$ is hydrogen or methyl;
- $A^2$ is hydrogen or methyl;
- n is 1, 2 or 3; and
- R is hydrogen, chlorine, bromince, hydroxy, methoxy, nitro, amino or trifluoromethyl.

8. A method according to claim 7 comprising the oral administration to humans of a compound of formula (III) in unit dosage form comprising from 0.01 to 100 mg of the said compound.

9. A method according to claim 7 comprising the oral administration to domestic mammals of from 0.025 mg/kg to 2.5 mg/kg of a compound of formula (III).

10. A compound according to claim 1 having the formula (IV):

$$R-\text{(benzofuran)}-CHOH-CH_2-NH-CH(CH_3)-CH_2-\text{(phenyl)}-CO_2H \quad (IV)$$

or an ester, amide or pharmaceutically acceptable salt of the carboxylic group thereof as defined in claim 1, wherein R is hydrogen.

* * * * *